United States Patent [19]

Hoskins et al.

[11] Patent Number: 5,922,540
[45] Date of Patent: Jul. 13, 1999

[54] MONOFUNCTIONAL GLYCOSYLTRANSFERASE GENE OF *STAPHYLOCOCCUS AUREUS*

[75] Inventors: Jo Ann Hoskins; Stanley R. Jaskunas, Jr., both of Indianapolis; Robert B. Peery, Brownsburg; Paul L. Skatrud, Greenwood, all of Ind.

[73] Assignee: Eli Lilly and Company, Indianapolis, Ind.

[21] Appl. No.: 08/771,716

[22] Filed: Dec. 20, 1996

[51] Int. Cl.[6] .......................... C12N 15/63; C12N 15/00; C12N 15/85; C07H 21/04
[52] U.S. Cl. ..................... 435/6; 435/320.1; 435/69.1; 435/252.3; 536/23.1; 536/23.5
[58] Field of Search ................... 435/69.1, 252.3, 435/6, 320.1; 536/23.1, 23.5

[56] References Cited

PUBLICATIONS

Paik et al, 1997, J. Bacteriol, 179(12): 4061–65.
Borchardt et al 1993. Gene 137:253–258.
M. Di Berardino, et al., "The monofunctional glycosyltransferase of *Escherichia coli* is a member of a new class of peptidoglycan–synthesising enzymes" *FEBS Letters,* 392, pp. 184–188, (1996).

*Primary Examiner*—Nita Minnfield
*Attorney, Agent, or Firm*—Mark J. Stewart; Thomas D. Webster

[57] ABSTRACT

The invention provides isolated nucleic acid compounds encoding a novel MTG of *Staphylococcus aureus*. Also provided are vectors and transformed heterologous host cells for expressing the MTG and a method for identifying compounds that bind and/or inhibit the enzymatic activity of the MTG.

16 Claims, 1 Drawing Sheet

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 807 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (ix) FEATURE:
      (A) NAME/KEY: CDS
      (B) LOCATION: 1..807

(xi) SEQUENCE DESCRIPTION: SEQ ID NO:1:

```
ATG AAA AGA AGC GAT AGG TAC TCA AAC TCA AAT GAA CAT TTT GAG CAT      48
Met Lys Arg Ser Asp Arg Tyr Ser Asn Ser Asn Glu His Phe Glu His
 1               5                  10                  15

ATG AAA CAC GAA CCT CAC TAT AAT ACG TAT TAT CAA CCA GTT GGC AAA      96
Met Lys His Glu Pro His Tyr Asn Thr Tyr Tyr Gln Pro Val Gly Lys
                20                  25                  30

CCG CCG AAA AAG AAA AAA AGT AAA CGA ATA CTA TTA AAA ATA TTA TTA     144
Pro Pro Lys Lys Lys Lys Ser Lys Arg Ile Leu Leu Lys Ile Leu Leu
        35                  40                  45

ACC ATT CTA ATC ATT ATC GCA TTG TTT ATT GGT ATC ATG TAT TTT TTA     192
Thr Ile Leu Ile Ile Ile Ala Leu Phe Ile Gly Ile Met Tyr Phe Leu
 50                  55                  60

TCT ACA CGC GAT AAT GTG GAT GAA CTA AGA AAA ATT GAA AAT AAA AGT     240
Ser Thr Arg Asp Asn Val Asp Glu Leu Arg Lys Ile Glu Asn Lys Ser
 65                  70                  75                  80

AGT TTT GTG TCA GCT GAT AAC ATG CCA GAG TAT GTT AAA GGT GCC TTT     288
Ser Phe Val Ser Ala Asp Asn Met Pro Glu Tyr Val Lys Gly Ala Phe
                85                  90                  95

ATT TCA ATG GAA GAT GAA CGA TTC TAC AAT CAT CAT GGA TTC GAT TTG     336
Ile Ser Met Glu Asp Glu Arg Phe Tyr Asn His His Gly Phe Asp Leu
        100                 105                 110

AAA GGT ACA ACT AGA GCT TTA TTT TCA ACG ATT AGC GAC AGA GAT GTG     384
Lys Gly Thr Thr Arg Ala Leu Phe Ser Thr Ile Ser Asp Arg Asp Val
115                 120                 125

CAA GGT GGT AGT ACC ATT ACA CAA CAA GTT GTC AAA AAT TAT TTT TAT     432
Gln Gly Gly Ser Thr Ile Thr Gln Gln Val Val Lys Asn Tyr Phe Tyr
130                 135                 140

GAT AAT GAT CGT TCA TTT ACT AGA AAA GTA AAA GAA TTA TTT GTA GCT     480
Asp Asn Asp Arg Ser Phe Thr Arg Lys Val Lys Glu Leu Phe Val Ala
145                 150                 155                 160

CAT CGA GTT GAA AAA CAA TAT AAT AAG AAC GAA ATT TTA AGC TTT TAT     528
His Arg Val Glu Lys Gln Tyr Asn Lys Asn Glu Ile Leu Ser Phe Tyr
                165                 170                 175

TTA AAT AAT ATT TAC TTT GGG GAT AAT CAA TAT ACG CTT GAG GGC GCA     576
Leu Asn Asn Ile Tyr Phe Gly Asp Asn Gln Tyr Thr Leu Glu Gly Ala
            180                 185                 190

GCA AAC CAT TAC TTT GGA ACA ACC GTG AAT AAA AAT AGT ACA ACA ATG     624
Ala Asn His Tyr Phe Gly Thr Thr Val Asn Lys Asn Ser Thr Thr Met
        195                 200                 205
```

-continued

```
TCT CAC ATA ACA GTT TTA CAA AGC GCT ATT TTA GCT AGT AAA GTC AAT       672
Ser His Ile Thr Val Leu Gln Ser Ala Ile Leu Ala Ser Lys Val Asn
    210                 215                 220

GCA CCT AGC GTA TAT AAT ATC AAT AAT ATG TCA GAG AAT TTT ACG CAA       720
Ala Pro Ser Val Tyr Asn Ile Asn Asn Met Ser Glu Asn Phe Thr Gln
225                 230                 235                 240

CGT GTA AGC ACG AAC TTA GAA AAA ATG AAG CAA CAA AAT TAT ATC AAT       768
Arg Val Ser Thr Asn Leu Glu Lys Met Lys Gln Gln Asn Tyr Ile Asn
                245                 250                 255

GAA ACA CAA TAT CAA CAG GCT ATG TCA CAA TTA AAT CGT                   807
Glu Thr Gln Tyr Gln Gln Ala Met Ser Gln Leu Asn Arg
                260                 265
```

(2) INFORMATION FOR SEQ ID NO:2:

(i) SEQUENCE CHARACTERISTICS:
        (A) LENGTH: 269 amino acids
        (B) TYPE: amino acid
        (D) TOPOLOGY: linear (ii) MOLECULE TYPE: protein (xi) SEQUENCE DESCRIPTION: SEQ ID NO:2:

```
Met Lys Arg Ser Asp Arg Tyr Ser Asn Ser Asn Glu His Phe Glu His
1                   5                   10                  15

Met Lys His Glu Pro His Tyr Asn Thr Tyr Tyr Gln Pro Val Gly Lys
                20                  25                  30

Pro Pro Lys Lys Lys Lys Ser Lys Arg Ile Leu Leu Lys Ile Leu Leu
                35                  40                  45

Thr Ile Leu Ile Ile Ile Ala Leu Phe Ile Gly Ile Met Tyr Phe Leu
    50                  55                  60

Ser Thr Arg Asp Asn Val Asp Glu Leu Arg Lys Ile Glu Asn Lys Ser
65                  70                  75                  80

Ser Phe Val Ser Ala Asp Asn Met Pro Glu Tyr Val Lys Gly Ala Phe
                85                  90                  95

Ile Ser Met Glu Asp Glu Arg Phe Tyr Asn His His Gly Phe Asp Leu
                100                 105                 110

Lys Gly Thr Thr Arg Ala Leu Phe Ser Thr Ile Ser Asp Arg Asp Val
                115                 120                 125

Gln Gly Gly Ser Thr Ile Thr Gln Gln Val Val Lys Asn Tyr Phe Tyr
130                 135                 140

Asp Asn Asp Arg Ser Phe Thr Arg Lys Val Lys Glu Leu Phe Val Ala
145                 150                 155                 160

His Arg Val Glu Lys Gln Tyr Asn Lys Asn Glu Ile Leu Ser Phe Tyr
                165                 170                 175

Leu Asn Asn Ile Tyr Phe Gly Asp Asn Gln Tyr Thr Leu Glu Gly Ala
                180                 185                 190

Ala Asn His Tyr Phe Gly Thr Thr Val Asn Lys Asn Ser Thr Thr Met
            195                 200                 205

Ser His Ile Thr Val Leu Gln Ser Ala Ile Leu Ala Ser Lys Val Asn
    210                 215                 220

Ala Pro Ser Val Tyr Asn Ile Asn Asn Met Ser Glu Asn Phe Thr Gln
225                 230                 235                 240

Arg Val Ser Thr Asn Leu Glu Lys Met Lys Gln Gln Asn Tyr Ile Asn
                245                 250                 255

Glu Thr Gln Tyr Gln Gln Ala Met Ser Gln Leu Asn Arg
                260                 265
```

-continued (2) INFORMATION FOR SEQ ID NO:3:

(i) SEQUENCE CHARACTERISTICS:
        (A) LENGTH: 807 base pairs
        (B) TYPE: nucleic acid
        (C) STRANDEDNESS: single
        (D) TOPOLOGY: linear (ii) MOLECULE TYPE: mRNA (iii) HYPOTHETICAL: NO (iv) ANTI-SENSE: NO (xi) SEQUENCE DESCRIPTION: SEQ ID NO:3:

```
AUGAAAAGAA GCGAUAGGUA CUCAAACUCA AAUGAACAUU UUGAGCAUAU GAAACACGAA      60

CCUCACUAUA AUACGUAUUA UCAACCAGUU GGCAAACCGC CGAAAAAGAA AAAAAGUAAA     120

CGAAUACUAU UAAAAAUAUU AUUAACCAUU CUAAUCAUUA UCGCAUUGUU UAUUGGUAUC     180

AUGUAUUUUU UAUCUACACG CGAUAAUGUG GAUGAACUAA GAAAAAUUGA AAAUAAAAGU     240

AGUUUUGUGU CAGCUGAUAA CAUGCCAGAG UAUGUUAAAG GUGCCUUUAU UUCAAUGGAA     300

GAUGAACGAU UCUACAAUCA UCAUGGAUUC GAUUUGAAAG GUACAACUAG AGCUUUAUUU     360

UCAACGAUUA GCGACAGAGA UGUGCAAGGU GGUAGUACCA UUACACAACA AGUUGUCAAA     420

AAUUAUUUUU AUGAUAAUGA UCGUUCAUUU ACUAGAAAAG UAAAAGAAUU AUUUGUAGCU     480

CAUCGAGUUG AAAAACAAUA UAAUAAGAAC GAAAUUUUAA GCUUUUAUUU AAAUAAUAUU     540

UACUUUGGGG AUAAUCAAUA UACGCUUGAG GGCGCAGCAA ACCAUUACUU UGGAACAACC     600

GUGAAUAAAA AUAGUACAAC AAUGUCUCAC AUAACAGUUU UACAAAGCGC UAUUUUAGCU     660

AGUAAAGUCA AUGCACCUAG CGUAUAUAAU AUCAAUAAUA UGUCAGAGAA UUUUACGCAA     720

CGUGUAAGCA CGAACUUAGA AAAAAUGAAG CAACAAAAUU AUAUCAAUGA AACACAAUAU     780

CAACAGGCUA UGUCACAAUU AAAUCGU                                        807
```

MONOFUNCTIONAL GLYCOSYLTRANSFERASE GENE OF *STAPHYLOCOCCUS AUREUS*

BACKGROUND OF THE INVENTION

This invention relates to recombinant DNA technology. In particular the invention pertains to the cloning of a gene, mtg, encoding a novel monofunctional glycosyltransferase, from *Staphylococcus aureus* and the use of said gene and its encoded protein in a screen for new inhibitors of bacterial cell wall biosynthesis.

The emergence of antibiotic resistance in common pathogenic bacterial species has justifiably alarmed the medical and research communities. The emergence and rapid spread of beta-lactam resistance has been particularly problematic. Increasingly, the only drug that can be used to treat infections with MDR (multiple drug resistant) organisms is vancomycin, and there is considerable concern that the bacteria could also develop resistance to vancomycin.

The bacterial cell wall comprises a peptidoglycan layer which provides mechanical rigidity for the bacterium. The peptidoglycan layer is composed of a sugar backbone (alternating residues of N-acetylglucosamine and N-acetylmuramic acid are polymerized through a transglycosylation reaction) attached to a pentapeptide (also referred to as "stem peptide") containing D and L amino acid residues. Adjacent stem peptide residues are covalently crosslinked during maturation of the peptidoglycan.

During formation of the mature peptidoglycan, a lipid-linked disaccharide-pentapeptide is translocated across the cytoplasmic membrane, exposing the pentapeptide sidechains to the cell surface. The fully mature peptidoglycan structure is obtained following transglycosylation and transpeptidation enzymatic reactions. Several enzymes appear to be involved in the transglycosylation and transpeptidation polymerizaion reactions, most notably the bifunctional high molecular weight PBPs. Interestingly, transglycosylation activity is also found in monofunctional enzymes known as monofunctional glycosyltransferases (MTG's). The MTG is a target for the development of new inhibitors of cell wall synthesis.

SUMMARY OF THE INVENTION

The present invention provides, inter alia, isolated nucleic acid molecules that encode an MTG from *Staphylococcus aureus*. The invention also provides protein products encoded by the gene, in substantially purified form.

Having the cloned mtg gene of *Staphylococcus aureus* enables the production of recombinant MTG protein and derivatives thereof for the implementation of assays and screens to identify new inhibitory compounds targeted at the peptidoglycan biosynthetic pathway.

In one embodiment the present invention relates to isolated gene mtg that encodes novel *Staphylococcus aureus* MTG, said gene comprising the nucleotide sequence identified as SEQ ID NO. 1.

In another embodiment the present invention relates to a novel protein molecule, MTG, wherein said protein molecule comprises the sequence identified as SEQ ID NO. 2.

In another embodiment, the present invention relates to a soluble form of MTG (designated MTG$^S$) wherein MTG$^S$ comprises amino acid residues 68 through 269 of SEQ ID NO.2.

In a further embodiment the present invention relates to a ribonucleic acid molecule encoding MTG protein, said ribonucleic acid molecule comprising the sequence identified as SEQ ID NO. 3 or fragment thereof.

In yet another embodiment, the present invention relates to a recombinant DNA vector that incorporates the *Staphylococcus aureus* mtg gene in operable linkage to gene expression sequences enabling said mtg gene to be transcribed and translated in a host cell.

In still another embodiment the present invention relates to homologous or heterologous host cells that have been transformed or transfected with a vector carrying the cloned mtg gene from *Staphylococcus aureus* such that said gene is expressed in the host cell.

In a still further embodiment, the present invention relates to a method for identifying compounds that bind and/or inhibit the enzymatic activity of the *Staphylococcus aureus* MTG protein or fragment thereof.

DESCRIPTION OF THE DRAWING

FIGURE. Plasmid pPSR-23, useful for high level expression of the *Staphylococcus aureus* mtg$^S$ gene of the present invention in the heterologous procaryotic host cell *Eschericia coli*.

DEFINITIONS

Figure 1:
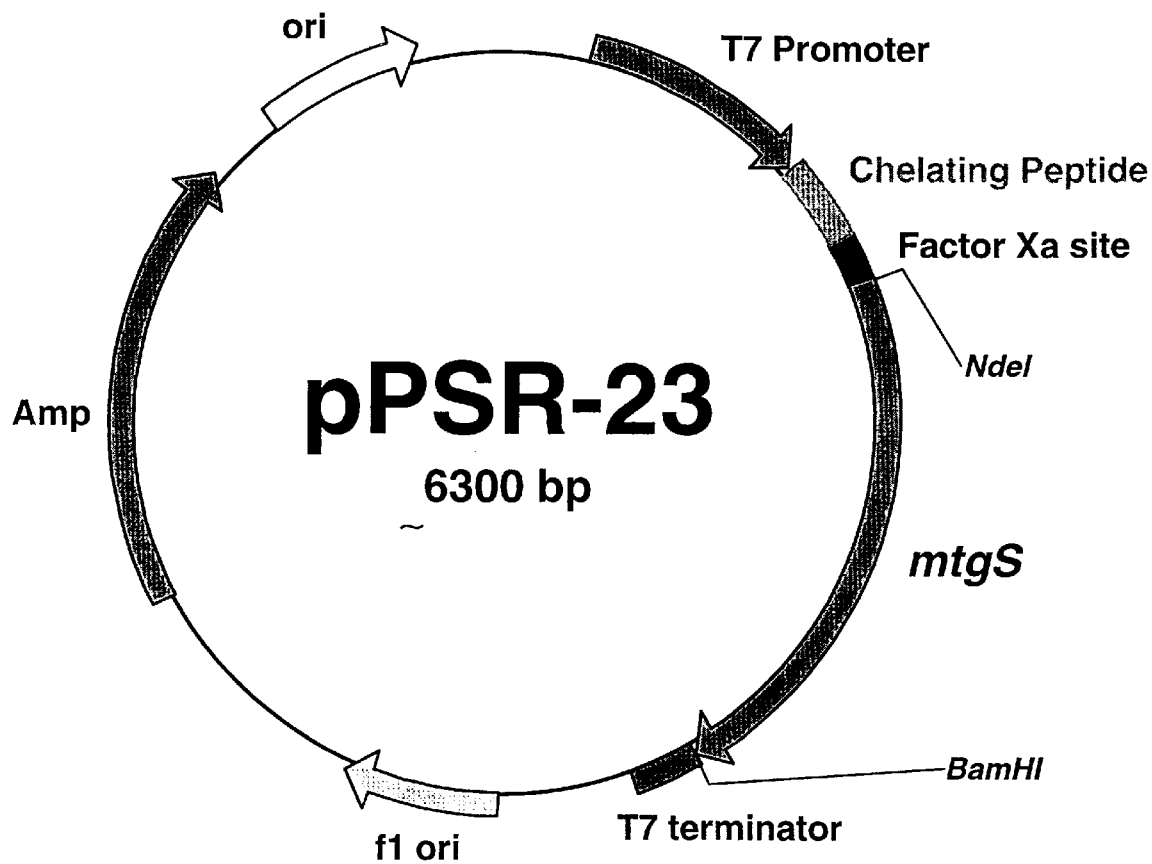

"mtg" refers to the *Staphylococcus aureus* genomic DNA sequence encoding MTG and fragments thereof.

"mtg$^S$" refers to a portion of mtg that encodes MTG$^S$ comprising nucleotide residues 202 through 807 of SEQ ID NO.1.

"MTG" as used herein may refer to the native monofunctional glycosyltransferase or to a portion thereof.

The terms "cleavage" or "restriction" of DNA refers to the catalytic cleavage of the DNA with a restriction enzyme that acts only at certain sequences in the DNA (viz. sequence-specific endonucleases). The various restriction enzymes used herein are commercially available and their reaction conditions, cofactors, and other requirements are used in the manner well known to one of ordinary skill in the art. Appropriate buffers and substrate amounts for particular restriction enzymes are specified by the manufacturer or can readily be found in the literature.

The term "fusion protein" denotes a hybrid protein molecule not found in nature comprising a translational fusion or enzymatic fusion in which two or more different proteins or fragments thereof are covalently linked on a single polypeptide chain.

"Functional domain" refers to a region of a protein having one or more distinct biological functions, for example, enzymatic activity, transmembrane anchoring, DNA binding, etc. A functional domain comprises a sequence of amino acids, the length of which and the identity of amino acid residues therein, may or may not be critical to said function.

The term "plasmid" refers to an extrachromosomal genetic element. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector, for example a plasmid or phage, in which a promoter and other regulatory elements are present to enable transcription of the inserted DNA.

The term "vector" as used herein refers to a nucleic acid compound used for introducing exogenous DNA into host cells. A vector comprises a nucleotide sequence which may encode one or more protein molecules. Plasmids, cosmids, viruses, and bacteriophages, in the natural state or which have undergone recombinant engineering, are examples of commonly used vectors.

The terms "complementary" or "complementarity" as used herein refers to the capacity of purine and pyrimidine nucleotides to associate through hydrogen bonding in double stranded nucleic acid molecules. The following base pairs are complementary: guanine and cytosine; adenine and thymine; and adenine and uracil.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation of, for example, a nucleic acid molecule.

The term "promoter" refers to a DNA sequence which directs transcription of DNA to RNA.

A "probe" as used herein is a labeled single-stranded nucleic acid compound of greater than 5 nucleotide residues that has the potential to hybridize with another nucleic acid compound.

The term "hybridization" as used herein refers to the phenomenon by which a single-stranded nucleic acid molecule joins with a complementary single-stranded nucleic acid molecule through nucleotide base pairing. "Selective hybridization" refers to hybridization that occurs under conditions of high stringency. The extent of hybridization depends upon a number of variable and constant parameters, for example, the degree of complementarity, the stringency of hybridization, and the length of hybridizing strands.

The term "stringency" refers to hybridization conditions. High stringency conditions disfavor non-homologous base-pairing. Low stringency conditions have the opposite effect. Stringency may be altered, for example, by changing the temperature and salt concentration.

"Transglycosylation" refers to an enzymatic reaction in which the sugar residues of lipid-linked disaccharide pentapeptide molecules are polymerized during the formation of the peptidoglycan structure of the bacterial cell wall.

DETAILED DESCRIPTION

The mtg gene (SEQ ID NO.1) of the present invention encodes a novel MTG enzyme of *Staphylococcus aureus* (SEQ ID NO. 2). The mtg gene disclosed herein comprises a DNA sequence of 807 nucleotide base pairs (SEQ ID NO. 1). There are no intervening sequences. Those skilled in the art will recognize that owing to the degeneracy of the genetic code (i.e. 64 codons which encode 20 amino acids), numerous "silent" substitutions of nucleotide base pairs could be introduced into the sequence identified as SEQ ID NO. 1 without altering the identity of the encoded amino acid(s) or protein product. All such substitutions are intended to be within the scope of the invention.

The MTG protein defined by SEQ ID NO.2 comprises a membrane-bound protein of 269 amino acid residues. The MTG protein of the present invention may be modified by deletion of amino acid residues 1 through 67 at the amino terminal end. Deletion of this region results in removal of the trans-membrane region and the production of a soluble form, $MTG^S$ which retains the transglycosylase domain of the native enzyme. Another modified form of MTG, which retains the transmembrane region, comprises amino acid residues 17 through 269 of SEQ ID NO.2.

Gene Isolation Procedures

Those skilled in the art will recogize that the gene of the present invention may be obtained by a plurality of applicable genetic and recombinant DNA techniques including, for example, polymerase chain reaction (PCR) amplification, or de novo DNA synthesis. (See e.g., J. Sambrook et al. *Molecular Cloning*, 2d Ed. Chap. 14 (1989)).

Methods for constructing gene libraries in a suitable vector such as a plasmid or phage for propagation in procaryotic or eucaryotic cells are well known to those skilled in the art. [See e.g. J. Sambrook et al. Supra]. Suitable cloning vectors are widely available.

Skilled artisans will recognize that the mtg gene of *Staphylococcus aureus* comprising the present invention or fragment thereof could be isolated by PCR amplification of *Staphylococcus aureus* genomic DNA or cDNA using oligonucleotide primers targeted to any suitable region of SEQ ID NO. 1. Methods for PCR amplification are widely known in the art. See e.g. *PCR Protocols: A Guide to Method and Application*, Ed. M. Innis et al., Academic Press (1990). The amplification reaction comprises genomic DNA, suitable enzymes, for example Taq DNA polymerase, primers, and buffers, and is conveniently carried out in a DNA Thermal Cycler (Perkin Elmer Cetus, Norwalk, Conn.). A positive result is determined by detecting an appropriately-sized DNA fragment following agarose gel electrophoresis.

Protein Production Methods

One embodiment of the present invention relates to the substantially purified MTG protein or fragment thereof, for example $MTG^S$.

Skilled artisans will recognize that the protein of the present invention can be synthesized by any number of different methods. The amino acid compounds of the invention can be made by chemical methods well known in the art, including solid phase peptide synthesis or recombinant methods. Both methods are described in U.S. Pat. No. 4,617,149, incorporated herein by reference.

The principles of solid phase chemical synthesis of polypeptides are well known in the art and may be found in general texts in the area. See, e.g., H. Dugas and C. Penney, *Bioorganic Chemistry* (1981) Springer-Verlag, New York, 54–92. For example, peptides may be synthesized by solid-phase methodology utilizing an Applied Biosystems 430A peptide synthesizer (Applied Biosystems, Foster City, Calif.) and synthesis cycles supplied by Applied Biosystems. Protected amino acids, such as t-butoxycarbonyl-protected amino acids, and other reagents are commercially available from many chemical supply houses.

The proteins of the present invention can also be produced by recombinant DNA methods using the cloned mtg gene or fragment thereof, as disclosed herein. Recombinant methods are preferred if a high yield of protein is desired. Expression of said cloned gene can be carried out in a variety of suitable host cells well known to those skilled in the art. In a recombinant method the mtg or $mtg^s$ gene or variants thereof are introduced into a host cell by any suitable means, well known to those skilled in the art. While chromosomal integration of a cloned mtg gene or variant thereof is within the scope of the present invention, it is preferred that the gene be cloned into a suitable extrachromosomally maintained expression vector so that the coding region of the gene is operably linked to a constitutive or inducible promoter.

The basic steps in the recombinant production of an MTG or MTG$^S$ of the present invention are:

a) constructing a natural, synthetic or semi-synthetic DNA encoding said MTG or MTG$^S$ protein;

b) integrating said DNA into an expression vector in a manner suitable for expressing said MTG or MTG$^S$;

c) transforming or otherwise introducing said vector into an appropriate eucaryotic or procaryotic host cell forming a recombinant host cell;

d) culturing said recombinant host cell in a manner enabling expression of said protein; and e) recovering and substantially purifying said protein by any suitable means, well known to those skilled in the art.

Expressing Recombinant MTG Proteins in Procaryotic and Eucaryotic Host Cells

In general, procaryotes are used for cloning DNA sequences and for constructing the vectors of the present invention. Procaryotes may also be employed in the production of the MTG proteins of the present invention. For example, the *Escherichia coli* K12 strain 294 (ATCC No. 31446) is particularly useful for the procaryotic expression of foreign proteins. Other strains of *E. coli,* bacilli such as *Bacillus subtilis,* enterobacteriaceae such as *Salmonella typhimurium* or *Serratia marcescans,* various Pseudomonas species and other bacteria, such as Streptomyces, may also be employed as host cells in the cloning and expression of the recombinant proteins of this invention.

Promoter sequences suitable for driving the expression of genes in procaryotes include β-lactamase [e.g. vector pGX2907, ATCC 39344, contains a replicon and β-lactamase gene], lactose systems [Chang et al., Nature (London), 275:615 (1978); Goeddel et al., Nature (London), 281:544 (1979)], alkaline phosphatase, and the tryptophan (trp) promoter system [vector pATH1 (ATCC 37695) which is designed to facilitate expression of an open reading frame as a trpE fusion protein under the control of the trp promoter]. Hybrid promoters such as the tac promoter (isolatable from plasmid pDR540, ATCC-37282) are also suitable. Still other promoters, such as that from bacteriophage T7, whose nucleotide sequences are generally known, enable one of skill in the art to ligate such promoter sequences to DNA encoding the proteins of the instant invention using linkers or adapters to supply any required restriction sites. Still other promoters are useful for gene expression in *S. pneumoniae,* for example the ami promoter (J. P. Claverys et al. "Construction and evaluation of new drug-resistance cassettes for gene disruption mutagenesis in *Staphylococcus aureus,* using an ami test platform," Gene (1995) 123–128). Promoters for use in bacterial systems will also contain a Shine-Dalgarno sequence operably linked to the DNA encoding the desired polypeptides. These examples are illustrative rather than limiting.

In addition to procaryotes, a variety of eucaryotic microorganisms such as yeast are suitable host cells. The yeast *Saccharomyces cerevisiae* is the most commonly used eucaryotic microorganism. A number of other yeasts such as *Kluyveromyces lactis* are also suitable. For expression in Saccharomyces, the plasmid YRp7 (ATCC-40053), for example, may be used. See, e.g., L. Stinchcomb, et al., Nature, 282:39 (1979); J. Kingsman et al., Gene, 7:141 (1979); S. Tschemper et al., Gene, 10:157 (1980). Plasmid YRp7 contains the TRP1 gene which provides a selectable marker for use in a trp1 auxotrophic mutant.

Purification of Recombinantly-Produced MTG and MTG$^S$

An expression vector carrying the cloned mtg or mtg$^S$ of *Staphylococcus aureus* or fragment thereof is transformed or transfected into a suitable host cell using standard methods. Cells that contain the vector are propagated under conditions suitable for expression of the encoded MTG. For example, if the gene is under the control of an inducible promoter, suitable growth conditions would incorporate an appropriate inducer. Recombinantly-produced MTG$^S$ or MTG protein may be purified from cellular extracts of transformed cells by any suitable means. Recombinantly-produced MTG that contains the N-terminal portion of the protein is expected to be localized in the host cell membrane. As such, recombinant MTGs may also be recoverable from cell extracts and cell membranes by any suitable means, well known to those skilled in the art.

In a preferred process for protein purification the gene encoding the MTG or MTG$^S$ of the present invention is modified at the 5' end to incorporate several histidine residues at the amino terminal end of the respective protein molecules. The "histidine tag" method enables a simplified protein purification known as "immobilized metal ion affinity chromatography" (IMAC), essentially as described in U.S. Pat. No. 4,569,794, which hereby is incorporated by reference. The IMAC method enables rapid isolation of substantially pure protein starting from a crude cellular extract.

Other embodiments of the present invention comprise isolated nucleic acid sequences. As skilled artisans will recognize, owing to the degeneracy of the genetic code the proteins of the invention can be encoded by a multitude of different nucleic acid sequences. Because these alternative nucleic acid sequences would encode the same amino acid sequences, the present invention further comprises these alternate nucleic acid sequences.

Nucleic acid sequences that encode SEQ ID NO:2 or subregion therein may be produced using synthetic methods. The synthesis of nucleic acids is well known in the art. See, e.g., E. L. Brown, R. Belagaje, M. J. Ryan, and H. G. Khorana, *Methods in Enzymology,* 68:109–151 (1979). The DNA segments corresponding to the mtg or related gene sequence mtg$^S$ could be generated using a conventional DNA synthesizing apparatus, such as the Applied Biosystems Model 380A or 380B DNA synthesizers (Applied Biosystems, Inc., 850 Lincoln Center Drive, Foster City, Calif. 94404) which employ phosphoramidite chemistry. Alternatively, phosphotriester chemistry may be employed to synthesize the nucleic acids of this invention. [See, e.g., M. J. Gait, ed., *Oligonucleotide Synthesis, A Practical Approach,* (1984).]

In an alternative and preferred methodology, namely PCR, the DNA sequence comprising a portion or all of SEQ ID NO:1 can be generated from *Staphylococcus aureus* genomic DNA using suitable oligonucleotide primers complementary to SEQ ID NO:1 or region therein, essentially as described in U.S. Pat. No. 4,889,818, which hereby is incorporated by reference. Suitable protocols for performing the PCR are widely known and are disclosed in, for example, *PCR Protocols: A Guide to Method and Applications,* Ed. Michael A. Innis et al., Academic Press, Inc. (1990).

The ribonucleic acids of the present invention may be prepared using the polynucleotide synthetic methods discussed supra, or they may be prepared enzymatically using RNA polymerase to transcribe a suitable DNA template.

The most preferred systems for preparing the ribonucleic acids of the present invention employ the RNA polymerase from the bacteriophage T7 or the bacteriophage SP6. These RNA polymerases are highly specific, requiring the insertion of bacteriophage-specific sequences at the 5' end of the template to be transcribed. See, J. Sambrook, et al., supra, at 18.82–18.84.

This invention also provides nucleic acids, RNA or DNA, that are complementary to SEQ ID NO:1 or SEQ ID NO:3.

The present invention also provides probes and primers useful for a variety of molecular biology techniques including, for example, hybridization screens of genomic or subgenomic libraries. A nucleic acid compound comprising SEQ ID NO:1, SEQ ID NO:3 or a complementary sequence thereof, or a fragment thereof, and which is at least 18 base pairs in length, and which will selectively hybridize to *Staphylococcus aureus* DNA or mRNA encoding the MTG or fragment thereof of the present invention, is provided. Preferably, the 18 or more nucleotide bases are DNA. These probes and primers can be prepared by enzymatic methods well known to those skilled in the art (See e.g. Sambrook et al. supra). In a most preferred embodiment these probes and primers are synthesized using chemical means as described above.

Another aspect of the present invention relates to recombinant DNA cloning vectors and expression vectors comprising the nucleic acids of the present invention. Many of the vectors encompassed within this invention are described above. The preferred nucleic acid vectors are those that comprise DNA. The most preferred recombinant DNA vectors comprise the isolated DNA sequence, SEQ ID NO:1. Plasmid pPSR-23 is an especially preferred DNA vector for expressing the soluble form of the MTG of this invention in *E. coli.*

The skilled artisan understands that choosing the most appropriate cloning vector or expression vector depends upon a number of factors including the availability of restriction enzyme sites, the type of host cell into which the vector is to be transfected or transformed, the purpose of the transfection or transformation (e.g., stable transformation as an extrachromosomal element, or integration into the host chromosome), the presence or absence of readily assayable or selectable markers (e.g., antibiotic resistance and metabolic markers of one type and another), and the number of copies of the gene to be present in the host cell.

Vectors suitable to carry the nucleic acids of the present invention comprise RNA viruses, DNA viruses, lytic bacteriophages, lysogenic bacteriophages, stable bacteriophages, plasmids, viroids, and the like. The most preferred vectors are plasmids.

When preparing an expression vector the skilled artisan understands that there are many variables to be considered, for example, whether to use a constitutive or inducible promoter. Inducible promoters are preferred because they enable high level, regulatable expression of an operably linked gene. The skilled artisan will recognize a number of inducible promoters that respond to a variety of inducers, for example, carbon source, metal ions, heat, and others. The practitioner also understands that the amount of nucleic acid or protein to be produced dictates, in part, the selection of the expression system. The addition of certain nucleotide sequences is useful for directing the localization of a recombinant protein. For example, a sequence encoding a signal peptide preceding the coding region of a gene, is useful for directing the extra-cellular export of a resulting polypeptide.

Host cells harboring the nucleic acids disclosed herein are also provided by the present invention. A preferred host is *E. coli* that has been transfected or transformed with a vector that comprises a nucleic acid of the present invention.

The present invention also provides a method for constructing a recombinant host cell capable of expressing SEQ ID NO:2, or the soluble form thereof, said method comprising transforming or otherwise introducing into a host cell a recombinant DNA vector that comprises an isolated DNA sequence which encodes SEQ ID NO:2 or fragment thereof. The preferred host cell is any strain of *E. coli* that can accomodate high level expression of an exogenously introduced gene. Preferred vectors for expression are those which comprise SEQ ID NO:1. An especially preferred expression vector for use in *E. coli* is pPSR-23, which comprises nucleotide residues 202 through 807 of SEQ ID NO:1. (See FIGURE). Transformed host cells may be cultured under conditions well known to skilled artisans such that a recombinant protein is expressed, thereby producing in the recombinant host cell the MTG or MTG$^S$ of the instant invention.

For the purpose of identifying or developing new antibiotic compounds it is useful to determine compounds that bind to MTG and/or inhibit the transglycosylase activity. The instant invention provides a screen for identifying compounds that inhibit the enzymatic activity of MTG or MTG$^S$ or fragment thereof, said screen comprising the steps of:

a) preparing and substantially purifying a recombinant MTG of the invention; alternatively, one can start with solubilized membranes from transformed cells;

b) exposing said MTG to a test compound; and c) monitoring, by any suitable means, the inhibition of enzymatic activity of said MTG by said compound.

The MTG or MTG$^S$ used in these experiments is preferably substantially purified as described herein. An alternative method for purifying membrane-bound MTG would comprise extraction from solubilized membrane preparations of cells transformed with the cloned mtg gene. Solubilized membranes are prepared according to well known methods.

The substrate for an MTG transglycosylase assay can be made according to art-recognized methods (See e.g. DiBerardino et al. FEBS Letters, 392, 184–88 (1996). For example, the lipid precursor substrate can be prepared from *Staphylococcus aureus* membranes, or from the membranes of any other suitable bacteria, UDP-Mur-Nac-pentapeptide, and UDP-N-acetyl-[$^{14}$C]glucosamine (Amersham, Buckinghamshire, UK). Transglycosylase activity is measured by the production of the peptidoglycan polymerization product essentially by mixing the substrate with a source of MTG and monitoring the amount of [$^{14}$C]-label in the peptidoglycan.

The screening system described above provides a means to determine compounds that interact with the MTG of the present invention and which may interfere with peptidoglycan biosynthesis. This screening method may be adapted to automated procedures such as a PANDEX® (Baxter-Dade Diagnostics) system, allowing for efficient high-volume screening for potential inhibitory agents.

The following examples more fully describe the present invention. Those skilled in the art will recognize that the particular reagents, equipment, and procedures described below are merely illustrative and are not intended to limit the present invention in any manner.

EXAMPLE 1

Construction of a DNA Vector for Expressing *Staphylococcus aureus* mtg$^S$ Gene in a Heterologous Host Plasmid pPSR-23 (See FIGURE) is an approximately 6300 base pair expression vector suitable for expressing a modified mtg$^S$ in procaryotic host *E. coli*. This plasmid contains an origin of replication (Ori), an ampicillin resistance gene (Amp), a T7 promoter, and a chelating peptide and Factor Xa site in operable linkage to the coding region of said mtg$^S$ gene. The chelating peptide and Factor Xa site are engineered onto the amino terminal end of the recombinant MTG$^S$ in order to simplify protein purification by providing a "his tag." (See Example 4). The parent plasmid of pPSR-23, pET16B (obtained from Novogen, Madison, Wis.), was digested with endonucleases NdeI and BamHI. Digested pET16B was ligated to a DNA fragment bearing NdeI and BamHI sticky ends, comprising a modified mtg$^S$ gene. The mtg$^S$ gene ligated into pPSR-23 encodes amino acid residues 68 through 269 of SEQ ID NO.2. The mtg$^S$ gene carried on pPSR-23 is most conveniently produced by PCR using standard methods and oligonucleotide primers targeted to the 5' and 3' ends of SEQ ID NO.1. The primer for synthesis at the 5' end of the gene is constructed to contain an NdeI site while the primer for synthesis at the 3' end of the gene is constructed to contain a BamHI site for cloning into pET16B.

EXAMPLE 2

Construction of a DNA Vector for Expression of mtg in a Heterologous Host

The plasmid construction method outlined in Example 1 is followed to construct a vector for expressing MTG comprising amino acid residues 17 through 269 of SEQ ID NO.2 in a heterologous host such as *E. coli*. Synthesis of the mtg gene used herein is most conveniently carried out by PCR on genomic DNA from *S. aureus*. Synthesis is primed at the 5' end of the gene starting at nucleotide position 49 of SEQ ID NO.1 using an appropriately synthesized oligonucleotide primer. This site comprises a natural NdeI site useful for cloning into plasmid pET16B. Synthesis at the 3' end of the mtg gene is primed using a primer constructed to contain a BamHI cloning site and targeted to nucleotide residues extending through nucleotide position 807 at the 3' end of SEQ ID NO.1.

EXAMPLE 3

Expression of *Staphylococcus aureus* mtgS Gene in *Echerichia coli*

Expression plasmid pPSR-23 was transformed into *E. coli* BL21 (DE3)pLys5(F$^-$ompT[lon]hsdS $r_B^-m_B^-$) using standard methods (See e.g. Sambrook et al. Supra). Transformants chosen at random were tested for the presence of pPSR-23 by agarose gel electrophoresis using quick plasmid preparations. Id. Transformants were grown overnight at 37° C. in LB medium supplemented with 100 μg/ml ampicillin. The overnight culture was diluted into fresh LB medium and allowed to grow to an O.D.$_{600}$ of 0.6 to 0.8. At that point, expression of the vector-bound mtgS gene was induced by adding 1.0 mM IPTG for a period of 4 hours. The induced-culture was then pelleted by centrifugation in preparation for protein purification (See Example 4).

EXAMPLE 4

Purification of MTG$^S$

The recombinant cell pellet, isolated as described in the last step of Example 3, was resuspended in 60 ml of 20 mM potassium phosphate, pH 7.5. The cells were disrupted by passage through a French press, producing a cell extract that was centrifuged at 150,000×g for 1 hour. The MTG$^S$ protein contained in the extract was purified by immobilized metal ion affinity chromatography (IMAC), essentially as described in U.S. Pat. No. 4,569,794, the entire contents of which is hereby incorporated by reference. Briefly, the IMAC procedure involved adding to the protein sample the following components at the indicated final concentrations: 0.5M NaCl, 5 mM imidazole. The sample was loaded onto a Chelating Sepharose Fast Flow column (Pharmacia, 10 ml bed volume) and the column washed twice with 35 ml each of 20 mM Tris, pH 8, 0.5 M NaCl and 5 mM imidazole; 20 mM Tris, pH 8, 0.5 M NaCl and 60 mM imidazole. The bound protein was eluted from the column with 20 mM Tris, pH 8, 0.5 M NaCl, 1 M imidazole.

EXAMPLE 5

Inhibition of MTG Transglycosylase Activity

Radiolabelled lipid precursor for use as substrate is prepared as described in H. Hara and H. Suzuki FEBS Lett. 168, 155–60 (1984). Peptidoglycan synthesis activities are determined in 50 μl reactions containing 50 nM PIPES, pH 6.1, 10 mM MgCl$_2$, 0.2 mM DTT, 1 mM ATP, 26% DMSO, MTG or MTG$^S$ sample and $^{14}$C-labelled lipid precursor. The reaction is incubated for 30 minutes at room temperature and filtered through hydrophilic Durapore PVDF membranes (0.65 μm; Millipore, Bedford, Mass.). Under these conditions the synthesized peptidoglycan is retained while the unincorporated labeled substrate is washed through using 0.4 M ammonium acetate in methanol. The filter-bound radioactivity is determined by scintillation counting.

Inhibition studies are carried out using the same reaction conditions described except that compounds to be studied for inhibitory activity are added to a final concentration between 1 mM and 10 mM.

We claim:

1. An isolated nucleic acid compound encoding a monofunctional glycosyltransferase from *Staphylococcus aureus*, said monofunctional glycosyltransferase consisting of the amino acid sequence which is SEQ ID NO:2.

2. An isolated nucleic acid compound encoding a monofunctional glycosyltransferase from *Staphylococcus aureus*, said monofunctional glycosyltransferase consisting of the amino acid sequence which is defined by residues 68 through 269 of SEQ ID NO:2.

3. An isolated nucleic acid compound consisting of a sequence encoding the protein of claim 1 or functional fragment thereof wherein said fragment retains peptidoglycan synthesizing activity.

4. An isolated nucleic acid compound of claim 1 wherein the sequence of said compound is SEQ ID NO:1 or a sequence complementary to SEQ ID NO:1.

5. An isolated nucleic acid compound of claim 1 wherein the sequence of said compound is SEQ ID NO:3 or a sequence complementary to SEQ ID NO:3.

6. A vector comprising an isolated nucleic acid compound of claim 1.

7. A vector comprising an isolated nucleic acid compound of claim 2.

8. A vector, as in claim 6, wherein said isolated nucleic acid compound is SEQ ID NO:1 operably linked to a promoter sequence.

9. A vector, as in claim 7, wherein said isolated nucleic acid compound consists of residues 202 through 807 of SEQ ID NO:1 operably linked to a promoter sequence.

10. An isolated host cell containing a vector of claim 6.

11. An isolated host cell containing a vector of claim 8.

12. An isloated host cell containing a vector of claim 9.

13. A method for constructing a recombinant host cell having the potential to express SEQ ID NO:2, said method comprising introducing into a host cell by any suitable means a vector of claim 6.

14. A method for expressing SEQ ID NO:2 in the recombinant host cell of claim 10, said method comprising culturing said recombinant host cell under conditions suitable for gene expression.

15. A method for constructing a recombinant host cell having the potential to express the amino acid sequence which is defined by residues 68 through 269 of SEQ ID NO:2, said method comprising introducing into a host cell by any suitable means a vector of claim 7.

16. A method for expressing residues 68 through 269 of SEQ ID NO:2 in the recombinant host cell of claim 15, said method comprising culturing said recombinant host cell under conditions suitable for gene expression.

* * * * *